(12) United States Patent
Derowe et al.

(10) Patent No.: US 7,396,359 B1
(45) Date of Patent: Jul. 8, 2008

(54) VASCULAR PORT DEVICE

(75) Inventors: Ari Derowe, Hatichon (IL); Amir Loshakove, Moshav Bazra (IL)

(73) Assignee: ByPass, Inc., Orangeburg, NY (US)

( * ) Notice: Subject to any disclaimer, the term of this patent is extended or adjusted under 35 U.S.C. 154(b) by 0 days.

(21) Appl. No.: 09/701,523

(22) PCT Filed: May 30, 1999

(86) PCT No.: PCT/IL99/00285

§ 371 (c)(1),
(2), (4) Date: Nov. 28, 2000

(87) PCT Pub. No.: WO99/62408

PCT Pub. Date: Dec. 9, 1999

(30) Foreign Application Priority Data

| May 29, 1998 | (IL) | 124694 |
| Mar. 19, 1999 | (IL) | 129067 |

(51) Int. Cl.
*A61B 17/04* (2006.01)

(52) U.S. Cl. .................................. 606/213
(58) Field of Classification Search .............. 606/213, 606/215, 216, 219, 153
See application file for complete search history.

(56) References Cited

U.S. PATENT DOCUMENTS

| 3,586,002 A | 6/1971 | Wood |
| 3,825,010 A | 7/1974 | McDonald |
| 4,069,826 A | 1/1978 | Sessions et al. |
| 4,366,819 A | 1/1983 | Kaster |
| 4,387,879 A | 6/1983 | Tauschinski |
| 4,485,816 A | 12/1984 | Krumme |
| 4,676,245 A | 6/1987 | Fukuda |
| 4,917,087 A | 4/1990 | Walsh et al. |
| 4,930,502 A * | 6/1990 | Chen ........................... 606/150 |
| 4,997,439 A | 3/1991 | Chen |
| 5,047,047 A * | 9/1991 | Yoon ........................... 606/216 |
| 5,127,412 A * | 7/1992 | Cosmetto et al. ............ 128/898 |
| 5,158,566 A | 10/1992 | Pianetti |
| 5,188,636 A | 2/1993 | Fedotov |
| 5,222,974 A | 6/1993 | Kensey et al. |
| 5,234,447 A | 8/1993 | Kaster et al. |
| 5,254,127 A | 10/1993 | Wholey et al. |
| 5,282,827 A | 2/1994 | Kensey et al. |
| 5,292,332 A | 3/1994 | Lee |
| 5,334,217 A * | 8/1994 | Das ............................. 606/213 |
| 5,478,353 A * | 12/1995 | Yoon ........................... 606/213 |
| 5,478,354 A * | 12/1995 | Tovey et al. .................. 606/219 |
| 5,486,187 A | 1/1996 | Schenck |

(Continued)

FOREIGN PATENT DOCUMENTS

DE 28 22 603 11/1979

(Continued)

*Primary Examiner*—Michael J. Hayes
*Assistant Examiner*—Nguyen Victor

(57) ABSTRACT

This invention is a device (210) for sealing a hole (100) in a blood vessel (102), comprising a blood vessel engager (217) having at least one spike (214), for engaging a portion of a blood vessel (102) adjacent a hole in the blood vessel, and a body (216) coupled to the blood vessel engager (217). The device (210) has at least two configurations, a first configuration in which the device does not seal the hole, and a second configuration to which the device can be changed so that the second configuration of the device seals the hole.

71 Claims, 11 Drawing Sheets

U.S. PATENT DOCUMENTS

| | | | | |
|---|---|---|---|---|
| 5,540,715 | A | 7/1996 | Katsaros et al. | |
| 5,618,311 | A | 4/1997 | Gryskiewicz | |
| 5,676,689 | A | 10/1997 | Kensey et al. | |
| 5,695,504 | A * | 12/1997 | Gifford et al. | 606/153 |
| 5,707,393 | A | 1/1998 | Kensey et al. | |
| 5,709,335 | A | 1/1998 | Heck | |
| 5,746,755 | A | 5/1998 | Wood et al. | |
| 5,759,194 | A | 6/1998 | Hammerslag | |
| 5,779,719 | A | 7/1998 | Klein et al. | |
| 5,792,173 | A | 8/1998 | Breen et al. | |
| 5,797,933 | A | 8/1998 | Snow et al. | |
| 5,814,005 | A | 9/1998 | Barra et al. | |
| 5,861,004 | A | 1/1999 | Kensey et al. | |
| 5,868,763 | A | 2/1999 | Spence et al. | |
| 5,910,155 | A * | 6/1999 | Ratcliff et al. | 606/213 |
| 5,935,147 | A | 8/1999 | Kensey et al. | |
| 5,941,890 | A * | 8/1999 | Voegele et al. | 606/151 |
| 5,948,425 | A | 9/1999 | Janzen et al. | |
| 5,964,782 | A | 10/1999 | Lafontaine et al. | |
| 5,976,159 | A | 11/1999 | Bolduc et al. | |
| 6,004,341 | A | 12/1999 | Zhu et al. | |
| 6,071,292 | A | 6/2000 | Makower et al. | |
| 6,197,042 | B1 * | 3/2001 | Ginn et al. | 606/213 |
| 6,391,036 | B1 | 5/2002 | Berg et al. | |
| 6,588,643 | B2 | 7/2003 | Bolduc et al. | |
| 7,060,084 | B1 * | 6/2006 | Loshakove et al. | 606/213 |

FOREIGN PATENT DOCUMENTS

| | | |
|---|---|---|
| DE | 31 47 609 | 6/1983 |
| EP | 0 744 237 | 5/1997 |
| EP | 0 774 237 | 5/1997 |
| WO | WO 97/07741 | 3/1997 |
| WO | WO 98/16161 | 4/1998 |
| WO | WO 98/32412 | 7/1998 |
| WO | WO 98/42262 | 10/1998 |
| WO | WO 01/19256 | 3/2001 |

* cited by examiner

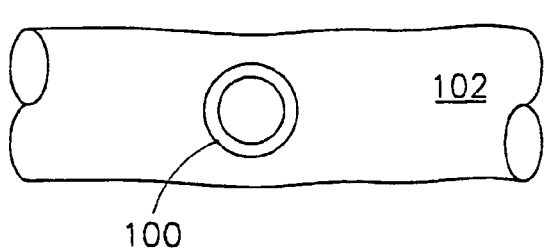
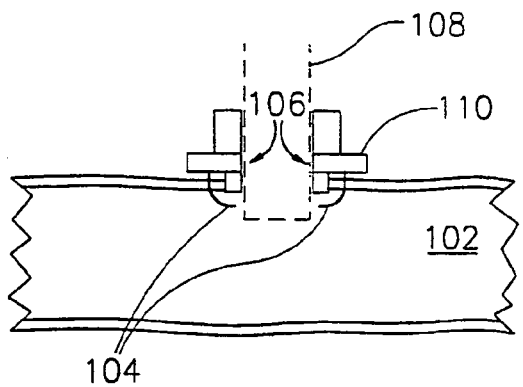
FIG.1A  FIG.1B
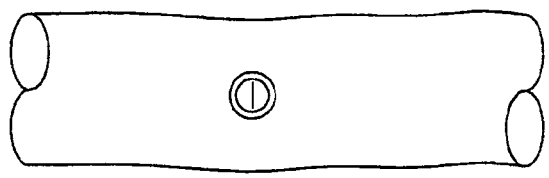
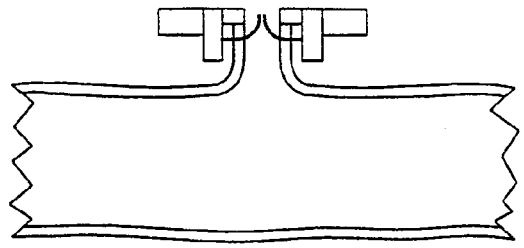
FIG.1C  FIG.1D
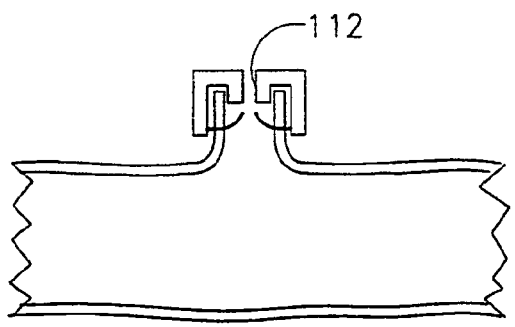
FIG.1E
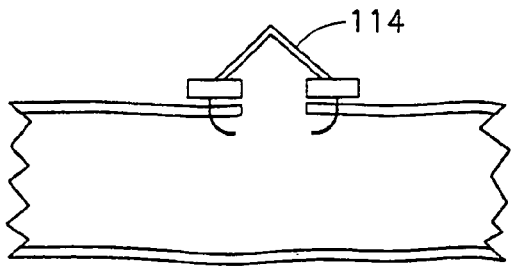
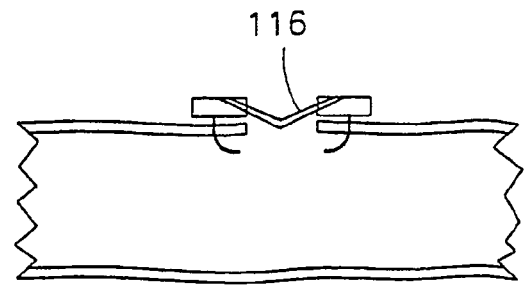
FIG.1F  FIG.1G

VASCULAR PORT DEVICE

FIELD THE INVENTION

Related Application

This application is a US national filing of PCT Application PCT/IL99/00285, filed May 30, 1999.

The present invention relates to vascular devices and especially to sealing vascular devices.

BACKGROUND OF THE INVENTION

There are many medical procedures in which a tube is temporarily inserted into- or out of-a blood vessel. One particular example is the use of a heart-lung machine during heart surgery. A first cannula is inserted into the aorta to return blood after it was oxygenated by the heart-lung machine. One or more second cannulas are inserted into the vena cava or the right atria. When the heart surgery is completed, the two cannulas are removed and the holes in the vena cava and aorta are closed using a "purse-string" suture, in which a single thread is stitched to surround the hole and then pulled tight (like a purse-string) to close the hole. Performing this suture requires skill and practice. In addition, it may be difficult to perform the suturing in a key-hole procedure or in other types of surgery where there is limited access to the wound site. Typically, the suture is attached as soon as the cannula is inserted into the body.

Another type of temporary tube insertion occurs during a failed anastomosis procedure. If the joining of two blood vessels fails, the point at which an opening (if any) was formed in one of the blood vessels, must be sutured shut, also possibly using a purse string.

Vascular ports, for example for the introduction of a catheter into a femoral artery, are known. Once the procedure is completed, the port is usually removed and the hole formed by the port is either sutured or closed using manual pressure. These ports are generally applied through the skin or a small incision and remain mostly outside the body.

SUMMARY OF THE INVENTION

An aspect of some preferred embodiments of the invention relates to a self-sealing anastomotic device. In a preferred embodiment of the invention, if an anastomosis cannot or is not completed, the device seals any opening in the vessel to which the device is connected. In a preferred embodiment of the invention, the device seals the opening by forcing the lips of the opening against each other or against a part of the device. Alternatively, the device seals the opening by forcing portions of the device against each other. In some embodiments of the invention, the anastomosis device severs a portion of one of the vessels of the anastomosis, for example an "end" vessel in an end-to-side anastomosis. Alternatively or additionally, the device, when it seals the opening, engages a larger portion of the blood vessel to which it is attached, to form a seal.

Alternatively to an integral device, the opening sealer may for an element which is brought over an existing anastomosis device or blood vessel, to seal the opening in the device or the blood vessel. In one example, the element comprises a collapsing ring which compresses the diameter of an anastomosis device and/or a blood vessel. Possibly, the element also severs a portion of the blood vessel, leaving only a stub, which stub is sealed. In some embodiments a double seal is formed, one at the severing location and one nearer to the blood.

In a preferred embodiment of the invention, a three configuration anastomosis device is provided. In a first configuration, the device is not deployed. In a second configuration, the device engages only one blood vessel. In a third configuration, the device either engages a second blood vessel or is sealed, depending on whether a second blood vessel is available and/or whether there is a tube or other spacer inserted in (or outside) the device when the device is changed from the second configuration to the third configuration. Alternatively, separate third and fourth configurations are provided. In the third configuration an anastomosis is performed in the fourth configuration the device is sealed. Preferably, the configuration to be used can be selected during the use of the device.

An aspect of some preferred embodiments of the invention relates to a self-sealing vascular port, at least a portion of which remains in the body after the usage of the port is completed to seal a hole in the vessel in which the port was inserted. In a preferred embodiment of the invention, the hole is sealed by portions of the device which are urged against each other. Alternatively, the hole is sealed by the device urging portions of the vessel against each other and/or against the device.

In a preferred embodiment of the invention, the port comprises a single element having both a sleeve function, to guide the insertion of objects into the port and a closure function to seal the hole when the port has completed its task. A valve function, for selectively allowing entry into the blood vessel may be integrated with the closure function or with the sleeve function, or may be a separate function. In some preferred embodiments of the invention, the valve can be opened by a tube pressing against it from outside the blood vessel or from inside the blood vessel.

Alternatively, the port comprises at least two portions, a removable sleeve portion and a closure portion which remains adjacent the blood vessel after the sleeve is removed.

An aspect of some preferred embodiments of the invention relates to a self-tightening purse-string attachment. In a preferred embodiment of the invention, the attachment is connected to one or more sutures which take part in a purse-string suture arrangement for closing a hole. When a tube inside the hole is removed, the attachment retracts the sutures, pulling the purse-string arrangement shut and thereby sealing the hole.

There is thus provided in accordance with a preferred embodiment of the invention, a device for sealing a hole in a blood vessel, comprising:

a blood vessel engager comprising at least one spike, for engaging a portion of a blood vessel adjacent a hole in the blood vessel; and a body coupled to the blood vessel engager, wherein said device has at least two configurations, a first configuration in which said device does not seal the hole and a second configuration to which said device can be changed, in which second configuration said device seals said hole. Preferably, said body defines a lumen therethrough. Preferably, said device comprises a second blood vessel engager for engaging a second blood vessel, such that the device can perform an anastomosis between said blood vessel and said second blood vessel.

Alternatively, said lumen is adapted to receive a tube therein, which lumen closes around said tube. Preferably, said body includes a valve for performing said closing. Alternatively or additionally, said body is radially compressed to perform said closing. Alternatively or additionally, said lumen is adapted for multiple insertions and removals of said tube. Alternatively or additionally, said lumen self-seals after said tube is removed.

In a preferred embodiment of the invention, said device is arranged to change configuration with less applied force, after said tube is removed.

In a preferred embodiment of the invention, said device is arranged to form said hole in said vessel. Alternatively or additionally, said at least one spike is arranged to engage said vessel after said hole has a final diameter, which final diameter is a diameter at which one or more tubes will be passed through said hole. Alternatively, said at least one spike is arranged to engage said vessel before said hole has a final diameter, which final diameter is a diameter at which one or more tubes will be passed through said hole. Alternatively, said at least one spike is arranged to engage said vessel before said hole is formed.

In a preferred embodiment of the invention, said at least one spike distorts when changing between said configurations. Alternatively or additionally, said configuration change comprises a distortion of said body. Alternatively or additionally, said at least one spike does not distort when changing between said configurations.

In a preferred embodiment of the invention, said body comprises a ring. Alternatively, said body comprises a hollow cylinder.

In a preferred embodiment of the invention, said configuration change comprises plastic distortion of at least part of the device. Alternatively or additionally, said configuration change comprises elastic distortion of at least part of the device. Alternatively or additionally, said configuration change comprises super-elastic distortion of at least part of the device. Alternatively or additionally, said configuration change comprises temperature-triggered shape-memory distortion of at least part of the device. Alternatively or additionally, in said second configuration, said at least one spike urges a first portion of said blood vessel against a second portion of said blood vessel, to seal said hole. Preferably, said device is arranged so that intimas of said two blood vessels are urged against each other to form said seal, by said configuration change.

In a preferred embodiment of the invention, said device is arranged so that in said second configuration, said at least one spike urges a first portion of said blood vessel against a portion of said device, to seal said hole. Alternatively, said device is arranged so that in said second configuration, a first portion of said device is urged against a second portion of said device, to seal said hole.

In a preferred embodiment of the invention, said device is adapted to be attached to a side of a blood vessel. Alternatively or additionally, said device is adapted to be attached to an end of a blood vessel.

In a preferred embodiment of the invention, said device is adapted to seal said hole and to remain in a body after a wound for accessing said device is closed. Preferably, said device remains at least two weeks in said body after said wound is healed. Alternatively or additionally, said body comprises a detachable portion which portion is removed prior to closing said wound.

In a preferred embodiment of the invention, said configuration change comprises a star distortion in which a circular profile of said body changes to a star profile. Alternatively or additionally, said configuration change comprises a rotational distortion in which a donut shaped body distorts around its median axis.

In a preferred embodiment of the invention, said seal comprises a single seal. Alternatively, said seal comprises a double seal.

There is also provided in accordance with a preferred embodiment of the invention, a method of providing a tool in a blood vessel of a patient, comprising:
attaching a port to the blood vessel;
using said port to access said blood vessel;
sealing said port; and
leaving said sealed port attached to said blood vessel for at least two weeks, wherein said port is completely enclosed by flesh of the patient. Preferably, removing a tube from said port causes said port to seal.

BRIEF DESCRIPTION OF THE DRAWINGS

The invention will be more clearly understood by reference to the following description of preferred embodiments thereof in conjunction with the figures, wherein identical structures, elements or parts which appear in more than one figure are labeled with the same numeral in all the figures in which they appear, in which:

FIGS. 1A-1D illustrates a self-sealing vascular port, in accordance with a preferred embodiment of the invention;

FIGS. 1E-1G illustrate various sealing mechanisms, in accordance with preferred embodiments of the invention;

DETAILED DESCRIPTION OF PREFERRED EMBODIMENTS

Figure 1H:
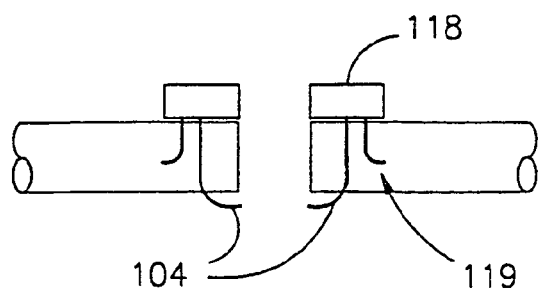
FIGS. 1H and 1I illustrate a port having two sets of spikes, in an open and a closed configuration, respectively, in accordance with a preferred embodiment of the invention.

FIGS. 1A-1D illustrate a self-sealing vascular port 100 in a vessel 102, in accordance with a preferred embodiment of the invention. FIGS. 1A and 1B illustrate a top view and a side cross-sectional view (respectively) of port 100, in an open configuration and FIGS. 1C and 1D illustrate port 100 in a sealed configuration. In the following figures, some changes have been made for clarity. For example, some of the "seals" are shown partly open, the degree of eversion is exaggerated in some figures, the length of spikes is sometimes exaggerated and the amount the spikes protrude from blood vessels is sometimes exaggerated. In the exemplary embodiment of FIG. 1, port 100 comprises a ring 110 having a plurality of spikes 104 to engage vessel 102. FIG. 1B shows port 100 being open and a tube 108 (dotted line) inserted in the opening of the port. In FIG. 1D, tube 108 is removed and port 100 changes configuration to become sealed, so no blood can exit from vessel 100. In the embodiments of FIG. 1A-1D, ring 110 rotates around its median axis, which axis is generally completely enclosed by the body of the ring, so that spikes 104, which engage vessel 102, urge portions of vessel 102 against each other. In this type of distortion, the ring does not move or rotate relative to the main axis (which is perpendicular to the blood vessel), but each circular cross-section of the ring rotates around the center of the cross-section. Preferably, an intima-to intima seal is achieved, however, this is not required in all preferred embodiments of the invention. In a preferred embodiment of the invention, once the port is sealed, the port remains in the body, possibly indefinitely.

Various mechanisms may be utilized to cause the change in configuration of port 100, including passive mechanisms, in which the port changes configuration by itself, active mechanisms in which the force is applied to the port and triggered mechanisms, in which a trigger is released by some means and the port then passively (or as a result of an outside force) distorts.

Passive mechanisms include for example, elasticity, super-elasticity and shape memory mechanisms. In one example, port 100 is pre-stressed to desire to achieve the configuration of FIG. 1D. However, as long as a tube 108 is inserted therein, this configuration cannot be achieved. Once the tube is removed, port 100 returns to the sealed configuration. In another example, the pressure of blood inside vessel 102 or the elasticity of vessel 102 causes configurational changes in port 100 (illustrated below).

Active mechanisms include, for example, applying force to distort port 100. In one a example, the force is applied by tube 108 during its removal. During which removal, the tube, if it engages the port, can, for example, plastically distort the port. In another example, the force is applied using a second device, for example a surrounding balloon (shown in FIG. 6D, below) which distorts the port and/or squeezes it shut. Such a surrounding balloon may form part of the port, such that the inflated balloon (possibly permanently inflated) maintains the port sealed. Alternatively the balloon may be used to plastically distort the port, after which distortion the balloon may be removed. Other types of forces can also be used to distort the port, including direct mechanical compression, for example using a pliers-like device.

Triggered mechanisms, include, for example a pin, which restrains the port from sealing. When the pin is removed, the port passively (or actively) distorts and seals (shown in FIG. 2, below). Alternatively, the removal of the pin allows the port to be distorted by an external balloon. In the case of FIG. 2, if the port does not distort by itself, the removal of the pin does make active distortion of the port easier (e.g., requiring less force).

Figure 1I:
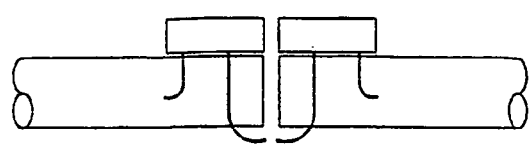
Figure 1J:
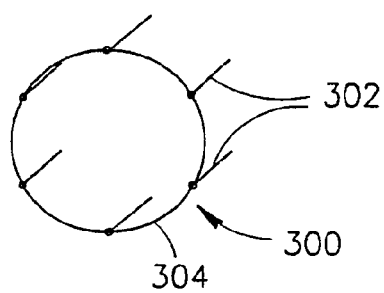
FIGS. 1J and 1K illustrate a port sealer in an open and a closed configuration, respectively, in accordance with a preferred embodiment of the invention.
Figure 1K:
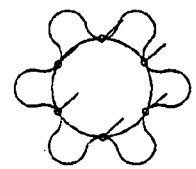
Figure 1L:
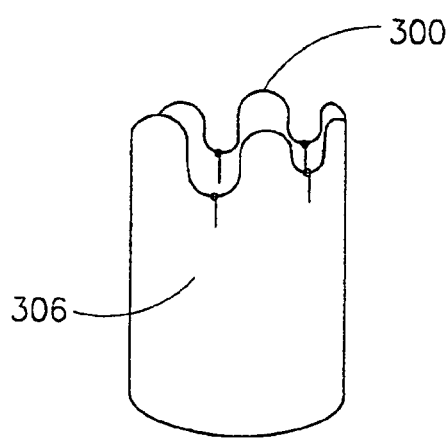
FIGS. 1L and 1M illustrate two alternative methods of manufacturing the port sealer of FIG. 1J.
Figure 1M:
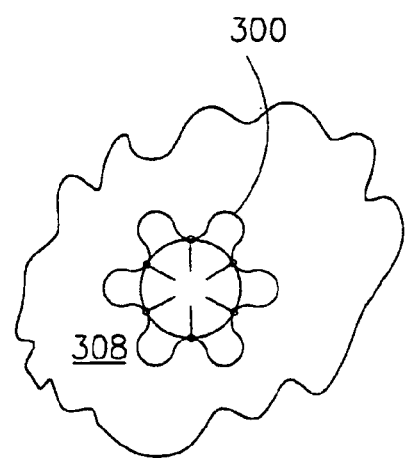
Figure 1N:
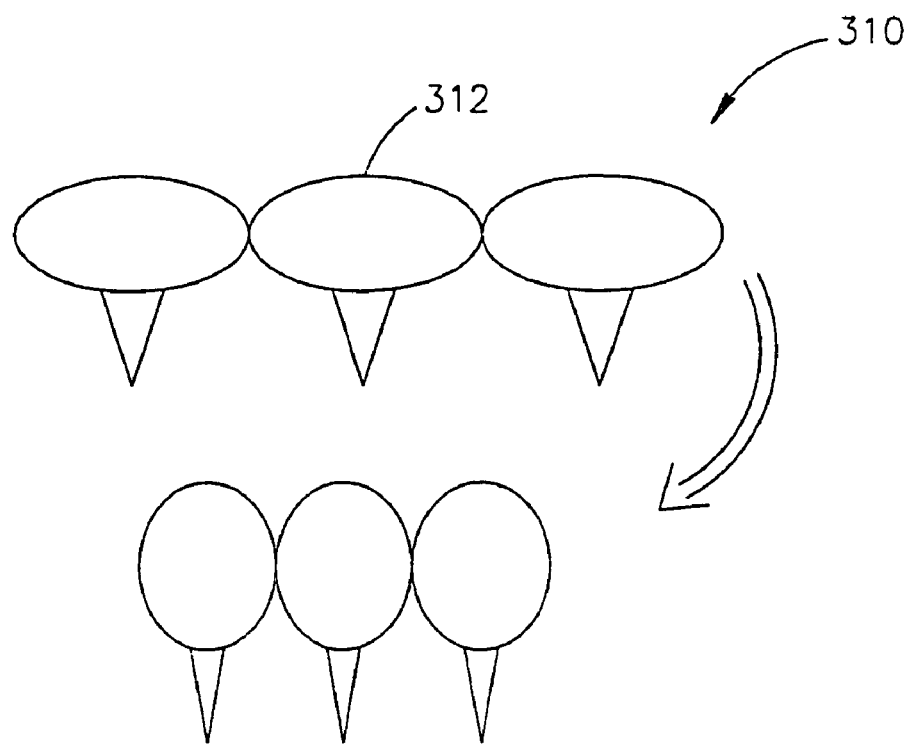
FIGS. 1N and 1O illustrate variations on the port sealer of FIG. 1J, in accordance with preferred embodiments of the invention.
Figure 8A:
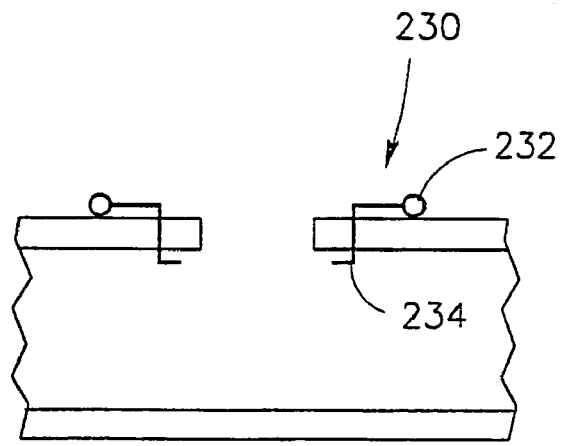
FIGS. 8A and 8B illustrates a hole sealer in which it is possible to avoid any contact between the sealer and the blood flow, in accordance with a preferred embodiment of the invention.
Figure 8B:
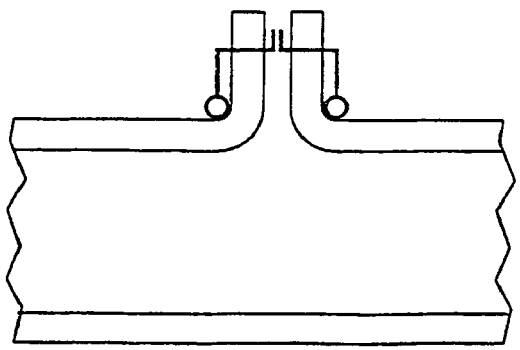
Figure 8C:
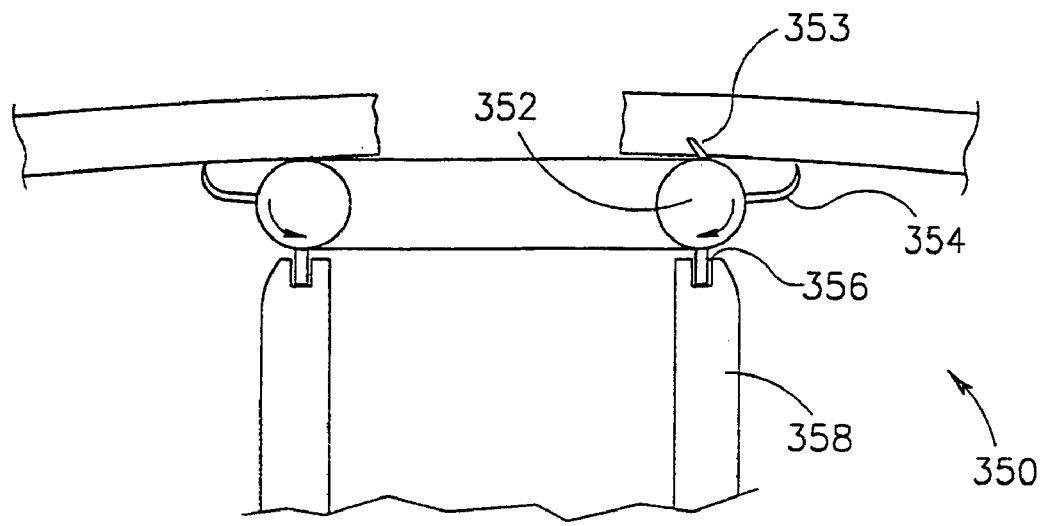
FIGS. 8C and 8D illustrate another hole sealer in which contact between the sealer and blood can be avoided, in accordance with a preferred embodiment of the invention.

As can be appreciated, various types of distortions of port 100 may be utilized, including the following (and combinations of the following) types of distortion:

(a) symmetric distortions, in which a similar distortion is applied to several parts of the port, for example a rotation around ring 110, an example of which is shown in FIG. 1N, below;

(b) asymmetric distortion, for example squeezing the port from a circular shape to an elliptical shape;

(c) rotational distortion, for example median-axis distortion as shown in FIGS. 1A-1D and in FIGS. in FIGS. 8B and 8C;

(d) iris-type distortion, in which the port, or at least parts of it collapse inwards like an iris;

(e) partial distortion, in which part of port 100 distorts and part remains stable, for example when the spikes are not distorted but their base is, or vice versa;

(f) various types of distortion of outlines, for example from an arc to a sine wave (FIG. 1J);

(g) spiral distortion, for example in FIG. 2, where the "coils" of the port tighten, thereby reducing its inner lumen; and (h) varying amounts distortion, like a star distortion shown in FIG. 1M, where only spiked portions of the ring distort, and other portions do not (or distort less) or vice-versa, with at least some of the spiked portions not distorting.

FIG. 1D illustrates an embodiment where the sealing of port 100 is achieved by portions of vessel 102 being urged against each other. FIG. 1E illustrates an alternative embodiment of the invention, in which port 100 includes an inner lip 112, which may be formed of one or more sections. When port 100 distorts, lips 112 press against each other (as shown in the Fig.) or against vessel 102, to form the seal of port 100.

FIG. 1F illustrates a port in which an external lip 114, formed for example of resilient rubber, creates a seal when an inserted tube is removed. In this example, substantially no distortion of port 100 is required.

FIG. 1G illustrates a port having an internal lip 116, in which the seal of the lip is enhanced by the internal pressure of vessel 102. Although FIG. 1G utilizes a mechanism similar to that of FIG. 1F, in which port 100 does not substantially distort, a same type of seal can be realized if port 100 distorts as in FIG. 1D (or in FIGS. 8C and 8D), but inwards, rather than outwards. In this variation, once lip 116 reaches the configuration shown in the Fig., the lip preferably cannot be pushed out of the blood vessel, due to a ratchet effect of the lip pressing against itself (or it may be formed of leaflets which press against each other) and/or due to a radius reduction (as in FIG. 8D) of the port, during the distortion.

The embodiment of FIG. 1G illustrates an optional feature of some preferred embodiments of the invention, in which the same port can be reused for inserting a second tube 108 from outside the blood vessel, by pressing the tube against lips 116. Thus, port 100 can be a single use port, for example for by-pass surgery, where, a heart-lung machine cannula is usually only inserted once. Alternatively, port 100 can be a multiple use port, for example during surgical procedures in which a plurality of catheters are inserted into or out of a blood vessel. Some types of ports described herein can also be used as permanent ports, such as for dialysis patients, however, these ports are especially suitable for short-duration uses, such as minutes, hours, days or weeks (such as 1, 2, 3 or 5 weeks), in which the "trouble" of removing the port and sealing the hole can be averted by some of the embodiments described herein.

Port 100, as described above can be designed to have only one set of spikes 104. When the port is distorted, all of the spikes move, as a group, to seal the port. FIGS. 1H and 1I illustrates an embodiment in which a port 118 includes at least two sets of spikes: a set 104 and a set 119, which sets move independently, with one set coming together to close the hole and another set 119 staying is place in moving in a different direction. A benefit of this type of multi-spike configuration is that the port maintains a fixed reference point relative to vessel 102, as well as or instead of relative to the sealed hole. Also, such a multi-spike embodiment may be useful for decoupling the sealing of the port from elastic and/or other tensions in vessel 102. Various mechanisms may be used for changing between the configurations of FIGS. 1H and 1I, for example, super elastic expansion of the base of the port or a balloon inflation mechanism such as in FIG. 6D.

In a preferred embodiment of the invention, once the utilization of port 100 is completed, port 100 is sealed. In a preferred embodiment of the invention, port 100 remains in the body. In some cases, it may be desirable to remove port 100, however, this is generally not required.

FIGS. 1J and 1K illustrate a port closing device 300, in accordance with a preferred embodiment of the invention. the device comprises a ring 304 having a plurality of spikes 302 attached thereto. In FIG. 1J the port closer is in an expanded (open configuration). The port closer is advanced in this configuration until the spikes engage a blood vessel. Then, ring 304 is distorted (as shown in FIG. 1K), so that spikes 302 move towards each other and pinch between them portions of the blood vessel, sealing the lumen of the port closer. Ring 304 is preferably formed of an elastic, super elastic and/or shape memory material, so that it is pre-disposed to collapsing in the absence of a restraint (such as a tube 108 inside of it). However, as described herein, the method of collapsing can include plastic deformation of the device by an external force or a combination of plastic- and other types of deformation.

FIG. 1L illustrates a method of manufacturing device 300, by cutting it out of a tube 306, for example using a wire EDM, a laser or a water jet. FIG. 1M illustrates an alternative method of manufacture, in which device 300 is cut out of a sheet 308. In some embodiments, the device is machined after it is cut, for example to remove burs or to roughen the surface. In a particular example, ring 304 is machined or otherwise worked to have a circular cross-section rather than a rectangular one.

FIG. 1N illustrates a portion of a device 310 which is a variation of device 300. The portion shown is a part of "ring" 304 and spikes attached thereto. Device 310 has ring 304 replaced by a series of distortable geometric shapes (cells) 312, such as ellipses (shown) or parallelograms. When the shapes are distorted, for example form that of a horizontal ellipse to that of a vertical ellipse, the circumference of the device is reduced, bringing the spikes closer together.

Figure 1O:
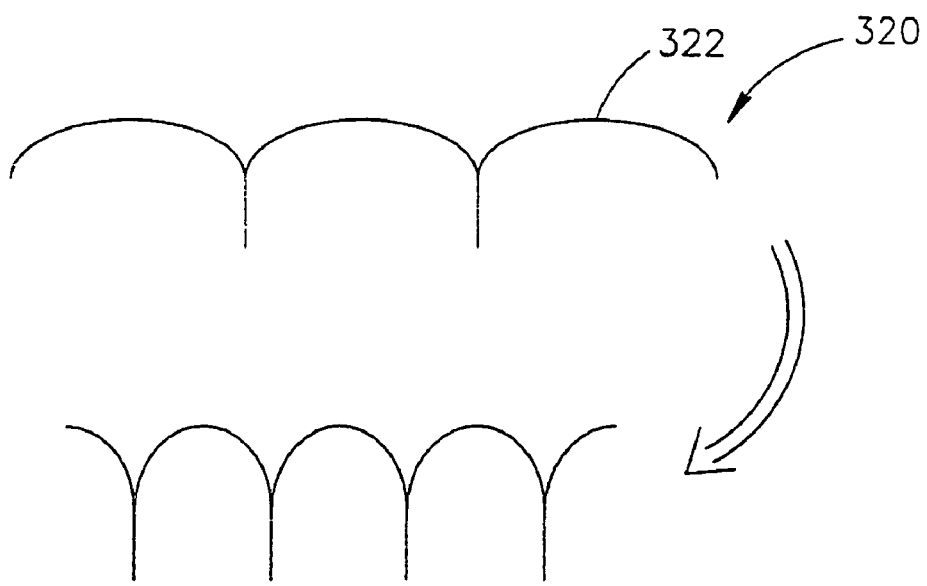

FIG. 1O illustrates a portion of a device 320 which is a variation of device 300, in which variation device 320 has ring 304 replaced by a series of arcs 312, which arcs can distort to have a greater curvature (and a smaller overall device circumference).

It should be noted that although the ring (or its replacement-variations) are shown as having a cross-section which is substantially perpendicular to the blood vessel surface, the ring-cross-section can be at other angles to the vessel, for example parallel to the vessel surface. Further, this angle can vary along the device or as a function of the deployment configuration of the device.

Figure 2A:
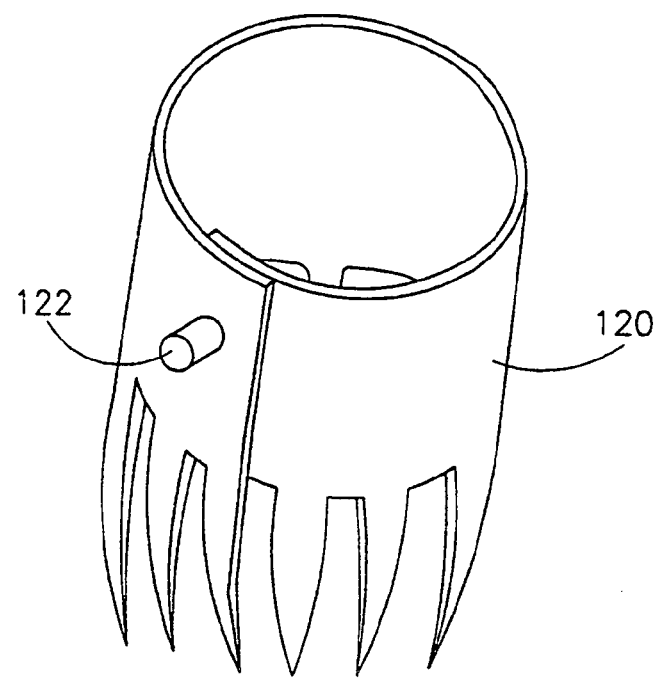
FIGS. 2A and 2B illustrate a port including a pin, in which the port seals, once the pin is removed, in accordance with a preferred embodiment of the invention.
Figure 2B:
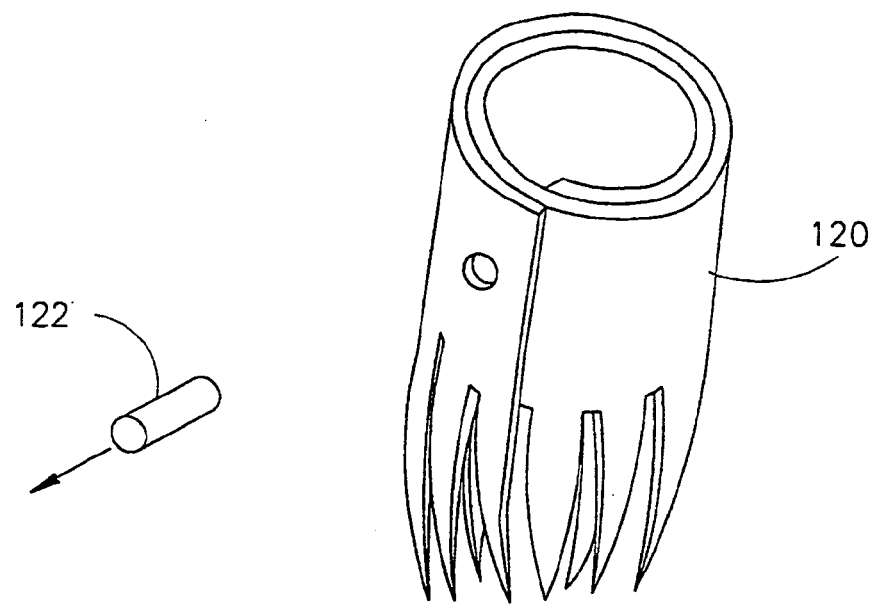

FIGS. 2A and 2B illustrates a port 120 including a pin 122. Once pin 122 is removed, port 120 seals at once, or seals once an internal tube is removed, and cannot be reopened. The sealing is preferably achieved by urging portions of the vessel which are engaged by the spikes of the port, towards each other. Alternatively, other methods of sealing the port, such as by applying an external force, may be used. Alternatively to a pin, the triggering of the sealing of port 120 may be achieved using a drawstring. Possibly, a time delay mechanism is used, to assure that all ports seal after a time, such a time-delay mechanism can include a bio-absorbable pin, which, when it is sufficiently absorbed or softened by being in the body, allows the port to distort.

In a preferred embodiment of the invention, port 100 includes a layer of clot inducing material outside the blood vessel, to induce clotting in any blood which escapes the seal. Such a layer may be provided as a coating on port 100. Alternatively or additionally, such a layer is provided during or after the deployment of port 100. Alternatively or additionally, port 100 includes an adhesive layer, to glue the lips of the port to each other and/or to the lips of vessel 102 at the hole that the port creates.

Figure 3:
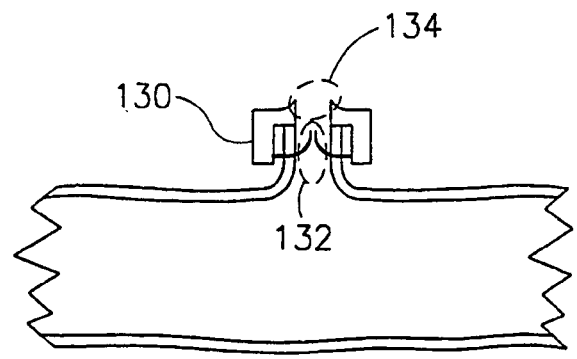
FIG. 3 illustrates a port having a two layer seal, in accordance with a preferred embodiment of the invention.

FIG. 3 illustrates a port 130 having a two layer seal, for example to provide added security against leakage. In the example of port 130, a first seal 132 is provided by urging portions of vessel 102 against each other. A second seal 134 is provided by urging outer lips of port 130 against each other.

As illustrated in FIG. 1A, the port includes a circular opening. However, in some embodiments of the invention, other shapes of openings may be useful, for example, ellipses, multiple holes, such as provided by a figure "S" or a key-hole cross-section and polygonal holes (for example triangular holes and square holes). The profile of the hole may be square, conical, hourglass or any other shape, for example by suitably forming the lips of port 100 or ring 110. Different port shapes are especially useful when the port is used for closing up a preexisting tear or other lesion of the vessel, in allowing the device to be matched to the lesion. In some embodiments of the invention, the inner lumen of the port is perpendicular to that of the blood vessel. In others, it may be parallel or at a different angle, for example less than 70°, less than 50° or less than 40°. Alternatively or additionally, the cross-section of the lumen is substantially the same as the outer cross-section of the port. Alternatively, the port may have a different shape and/or have a considerable thickness, so that the cross-sections are not the same.

The lips of the port may be formed of a continuous ring. In some embodiments, the lips 1, are formed of a plurality of overlapping or non-overlapping leaflets. The overlapping may be at the sides of the leaflets and/or at the tips of the leaflets. In some preferred embodiments of the invention, a leaflet includes one or more crevices and/or protrusions to engage other leaflets and aid in forming the seal.

In a preferred embodiment of the invention, the port is formed of hard material, such as a metal, for example stainless steel or an NiTi alloy or a plastic. Alternatively or additionally, the port is formed of a soft material, such as a silicon rubber. In various preferred embodiments of the invention, the port, or parts thereof, exhibit elastic, super elastic, plastic and/or shape memory properties. In some preferred embodiments of the invention, the port is formed of a rigid frame which is coated with a soft layer, such as silicon rubber. The frame preferably provides the ability for the port to passively or actively distort and the silicon preferably provides a resilient seal and/or a pressure distributing means.

In some preferred embodiments of the invention, the port is formed of bio-absorbable materials, preferably, so that after a time the port dissolves or is otherwise broken down, completely, or at least in part.

A PCT application titled "Methods and Devices for Vascular Surgery", filed on even date with the instant application in the Israel receiving office of the PCT and having same applicants, the disclosure of which are incorporated herein by reference, describes various anastomotic connectors. Some of these anastomotic connectors include a mechanism for engaging a blood vessel, entering (or exiting) the blood vessel, and/or maintaining a hole in a blood vessel. In a preferred embodiment of the invention, these mechanisms are utilized for providing and/or using a self-sealing port, as described herein.

One or more of the following issues are preferably taken into account when designing and/or selecting a device for sealing a port. These issues are listed in a general order corresponding to the steps of using such a device.

A first issue is bringing the port to the blood vessel. In a preferred embodiment of the invention, a port is brought to a blood vessel using a catheter (inside the blood vessel) or an endoscope (from outside the blood vessel). In some cases, the port is used in a surgical procedure in which the access to the blood vessel is a keyhole surgical wound or a standard surgical wound. Preferably, the port is formed of an elastic material so that it can be radially and/or axially compressed during the provision of the port.

A second issue is engaging the blood vessel by the port. In a preferred embodiment of the invention, the port includes spikes which, can be selectively bent (or released) when the port is brought into contact with the blood vessel, thereby engaging the vessel. Alternatively or additionally, the port may be sutured to the vessel, preferably using a minimally invasive technique, for example as described in PCT publication WO 98/42262, the disclosure of which is incorporated herein by reference. Alternatively or additionally, the engaging is integrated with the hole making, described below. In a preferred embodiment of the invention, the port is provided in a first undistorted configuration. When the port is placed against the vessel, the port (or part of it) is distorted, thereby allowing the spikes to engage the vessel. Sealing the port is preferably achieved by further distorting the port. Alternatively, in some configurations, if the port is distorted using a force opposite to the one which caused the distortion in the first place, the port seals, rather than being removed (for example utilizing a structure such as in the embodiments of FIGS. 1H and 11). In some preferred embodiments of the invention, the blood vessel is engaged using a suction source provided at port 100.

Engaging the blood vessel may be achieved by various mechanisms for folding, extending and bending spikes while deploying an implantable device. As described in the above PCT application of even date, spikes can be bent using many mechanisms, including elasticity, cantilevering, twisting and bending by force.

A third issue is forming the hole in vessel 102. In a preferred embodiment of the invention, the hole is formed using a sharp tip or a knife, possibly provided using the same means as the port, and/or provided through the opening in the port. Alternatively, the port itself, for example in a first, distorted configuration, has a sharp tip which forms the hole. For example, in the embodiment of FIG. 1J, if the device is provided to the vessel in a collapsed configuration with the spike tips overlapping (forming a general shape of a cone), the hole may be formed by expanding the device after the cone pokes into the blood vessel. Once the device is expanded, a tube may be placed in the hole and the device retracted and then advanced, so that the spikes can engage the vessel, individually. Alternatively, a device as shown in the above referenced PCT application of even date may be used, in which the spikes first cut the hole and then distort or move to engage the blood vessel. Alternatively or additionally, to cutting, a hole may be formed using a punch, possibly utilizing the body of port 100 as part of the punch, for example as the punch's anvil.

A fourth issue is expanding a hole in vessel 102 to the desired size of the port. In some cases, the hole is formed at its full size. However, in other cases, the formed hole is small and needs to be expanded. In a preferred embodiment of the invention, the hole is expanded using a balloon which is inflated in the hole. Alternatively or additionally, the hole is expanded by causing spikes 104 which engages vessel 102 to travel away from each other, thereby expanding the hole. It should be appreciated that the engagement of vessel 102 may possibly proceed in several steps or may occur only after the hole is formed. In one example, spikes 104 engage vessel 102 only after the hole is formed and then expanded using a balloon. A different set of spikes (if any) may be used for the primary engagement of the vessel, in which engagement the port is coupled to the vessel.

A fifth issue is maintaining the hole in vessel 102. In some cases, for example in some types of passive ports, the port, if left alone, seals the port. The hole is preferably maintained by restraining the port from closing, for example by inserting tube 108 therethrough. Alternatively, the port comprises a bi-stable configuration, with the stable states being "open" and "closed". A bi-stable element is described in PCT publication WO 98/32412, the disclosure of which is incorporated herein by reference. In this PCT publication, a stent with two stable radii is described. A similar configuration as the stent, but including spikes at one end thereof (as in FIG. 2, for example) can be used to provide a port and then seal it, in accordance with a preferred embodiment of the invention. The spikes engage the blood vessel. when the port is changed to a smaller diameter stable state the spikes move towards each other urging the lips of the hole in the vessel against each other and sealing the hole. The above PCT also describes a bi-stable valve. However, unlike the valve described there, in the present embodiment, the bi-stable element is used to selectively reduce the radius of the entire lumen, for the purpose of sealing the lumen. In the PCT publication, the bi-stable element is either used to compresses a stent (without sealing the lumen and without causing spike-engaged portions of the vessel to abut) or to move a valve element against a specially formed valve.

In the bi-stable embodiment of present invention, once the port is in the open state, it will tend to stay open, unless the port is shifted to the closed state. Alternatively to a bi-stable mechanism, a ratchet based mechanism may be used, either to create a "normally open" port or a "normally closed" port. Once the port is in one state, the ratchet latches and the port can change configuration only by application of a large force or by releasing the latch (for example a pin as described in FIG. 2).

A sixth issue is distorting the port or parts thereof. The above PCT application of even date describes various mechanisms of distorting an implant, including shape-memory, balloons, including balloons or other distorting tools, possibly with fingers for pressing against particular points on the port structure, and bi-stable structures. Any of these mechanisms may be applied towards constructing a port in accordance with a preferred embodiment of the invention. It should be appreciated that different parts of the port, for example the ring and the spikes, or individual spikes, may be distorted in different ways and by different amounts. Further, a same part of the port may be distortable in more than one way.

A seventh issue is how much of the port remains in contact with the blood flow after the port is sealed. As can be seen in various embodiments described herein, the contact area can be large, for example the entire size of the hole. Alternatively it can be small, for example is the hole is shrunken by the closure of the port. It can be minuscule, for example if only small portions of the spikes remain in the blood stream or no contact can remain, for example if the spikes do not penetrate to the inside of vessel 102 or if the portion which is penetrated is outside the seal. By suitable distortion of the port, a port may be applied from inside a blood vessel and then seal such that most or all of the port is outside the blood vessel.

An eighth issue is the amount of eversion caused by the port. Two measures of eversion can be recognized, the angle between the everted portion and the rest of the vessel and the length of vessel which is everted out of the plane of the vessel surface. In various embodiments described herein, different degrees of both measures may be achieved. In some cases, for example in Aortic hole-closing, it may be desirable to minimize both measures of eversion.

A ninth issue is the profile of the closed hole. The profile depends both on the eversion and on the shape of the port when it is sealed. In some applications, it is desirable that the port be as flush as possible with the vessel surface, lack and sharp edges and/or have a minimum effect on the inner lumen of the blood vessel. In other applications some or all of these features are not required. In some embodiments described herein, the port may be axially compressed or its protruding lips cut off or folded down, to minimize the protrusion of the device from the vessel surface. This further distortions may be passive, active, triggered by the collapsing of the device, and/or meditated by a time delay, such as by the dissolution of bio-absorbable pins holding the port together.

A tenth issue relates to the relative distortion and/or motion of the spikes as compared to the body of the device. In some embodiments, the spikes move independently of the ring, for example bending and/or unfolding. In other embodiments, it is the ring that distorts with a possible result of movement of the spikes. In other embodiments, various combinations of the rings distorting and the spikes distorting may be employed.

The above devices have been described mainly as temporary ports. However, it is noted that when an anastomosis is made, and fails to be completed, the effect is similar to that of a port. In a preferred embodiment of the invention, an anastomosis device is provided that self-seals if the anastomosis is not completed. Various embodiments of anastomosis devices are described in the above referenced PCT application of even date.

Figure 4:
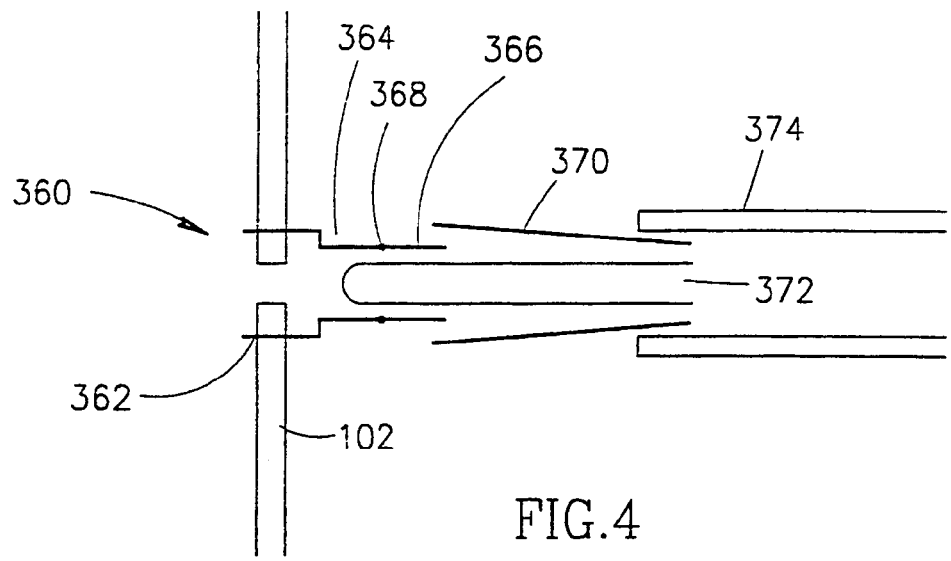
FIG. 4 illustrates an anastomosis connector which selectively seals or completes an anastomosis, in accordance with a preferred embodiment of the invention.

FIG. 4 illustrates a side cross-sectional view of an anastomosis device 360 which can be used to selectively seal itself or complete an anastomosis. Device 360 comprises a plurality of spikes 362 which engage vessel 102 and a cylindrical sleeve, comprising a proximal (to the spikes) portion 364 and a distal portion 366. The two portions are bridged by a pivot 368. In an anastomosis mode of operation, an inner mandrel, such as a catheter 372 is provided in the lumen of port 360, adjacent to proximal portion 364. A blood vessel 374 is brought over distal portion 366 and then the radius of the distal portion is increased to engage the blood vessel. As described in the PCT application filed on even date, this increase in radius can also cause spikes to extend from portion 366 into vessel 374. The increase in radius can be, for example, by inflating a balloon inside the lumen, adjacent portion 366 or by portion 366 being having a resting configuration with a larger radius, which configuration is prevented from being achieved by a restraint, such as an outer tube 370. Once the restraint is removed, the radius of distal portion 366 increases and the anastomosis is completed. The cross-section of proximal portion 364 is preferably not affected because its shape is maintained by catheter 372. Therefor, in a preferred embodiment of the invention, some amount of plastic deformation is achieved at pivot 368.

If an anastomosis in not desired, for example if vessel 374 fails at its other end, vessel 374 is not provided and neither is catheter 372 (at least not to proximal portion 364). Pivot 368 preferably comprises a ring which is restrained from having its radius change. Thus, when the radius of portion 366 is increased, pivot 368 transfers the force to portion 364, whose radius decreases, causing the port to seal, for example by the spike moving towards each other. Preferably, the materiel characteristics of pivot 368, distal portion 366 and proximal portion 364 are selected so that pivot 368 (and not portion 366) will plastically distort under the force of the expansion of portion 366. However, pivot 368 is preferably strong enough to resist plastic deformation at a force which is strong enough to distort the most proximal section of proximal portion 364, so that moving of the spikes is a preferred occurrence to plastic distortion at the pivot.

Figure 5:
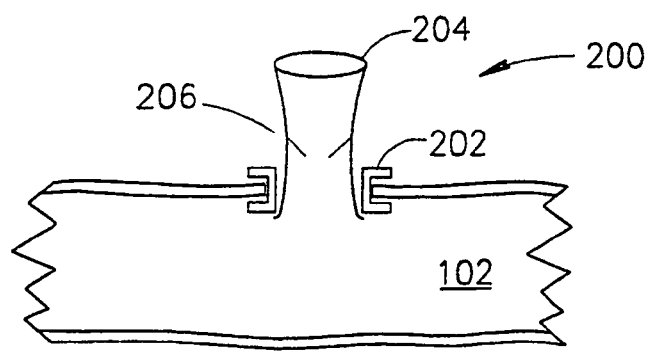
FIG. 5 illustrates a two part port, comprising a sleeve and a sealing portion, in accordance with a preferred embodiment of the invention.

FIG. 5 illustrates a two part port 200, comprising a short sleeve 204 and a sealing portion 202. During operation of the port, a tube (not shown) can be brought into (or out of) blood vessel 102 through sleeve 204. When the usage of port 200 is completed, sleeve 204 is removed and sealing portion 202 is closed (actively, passively or triggered), thus sealing the hole is vessel 102. Optionally, a valve portion 206 is provided, to prevent the loss of blood when there is no tube in vessel 102. Preferably, sealing portion 202 remains in vessel 102 after the procedure is completed.

Figure 6A:
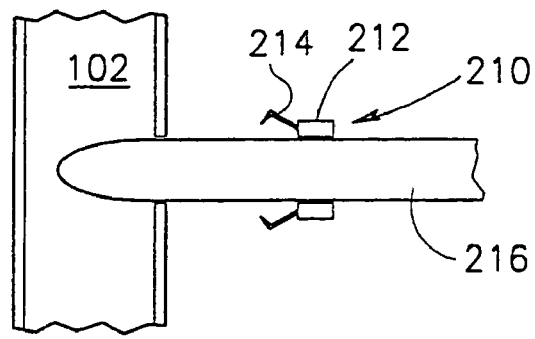
FIG. 6A illustrates a port sealer, which is brought over a catheter or other tool to a hole in a blood vessel and, when deployed, seals the hole.

FIG. 6A illustrates a port sealer 210, which is brought over a catheter or other tool to a hole in a blood vessel and, when deployed, seals the hole. As used herein the term "deployed" means that the device is attached and activated so that it performs at least one of its functions. In the example of FIG. 6, port sealer 210 comprises a ring portion 212 and a plurality of spikes 214. It should be noted that many devices described herein may be used alternatively as ports or as hole closures. In some embodiments, a port may be brought over a catheter to close an existing hole. Generally, the distinction between ports and hole closures is one of specialization: a hole closed can be more easily provided over a catheter and may be more difficult to work through. In addition, devices which include additional functions, such as valves may be limited to only one use. In a preferred embodiment of the invention, sealer 210 is brought over a catheter 216 towards vessel 102. Spikes 214 engage vessel 102. The catheter is preferably retracted at least out of the lumen of the blood vessel. Sealer 210 (or ring 212 thereof) is then (or at the same time) distorted, bringing spikes 214 towards the center of the hole and sealing the hole (once catheter 216 is removed).

As shown in FIG. 6A, the outer diameter of sealer 210 is substantially greater than that of catheter 216. In a preferred embodiment of the invention, a sealer having a substantially same diameter as the catheter is provided. In one preferred embodiment of the inventions, spikes 214 are formed to desire elastically to touch or cross each other. Spikes 214 are forced apart enough so that they fit over the diameter of catheter 216. Once the spikes engage vessels 102, catheter 216 is removed and the spikes fold in to seal the hole. In another embodiment of the invention, spikes 214 are folded in by an action of inflating a balloon in (or releasing a restraint) on ring 212.

Figure 6B:
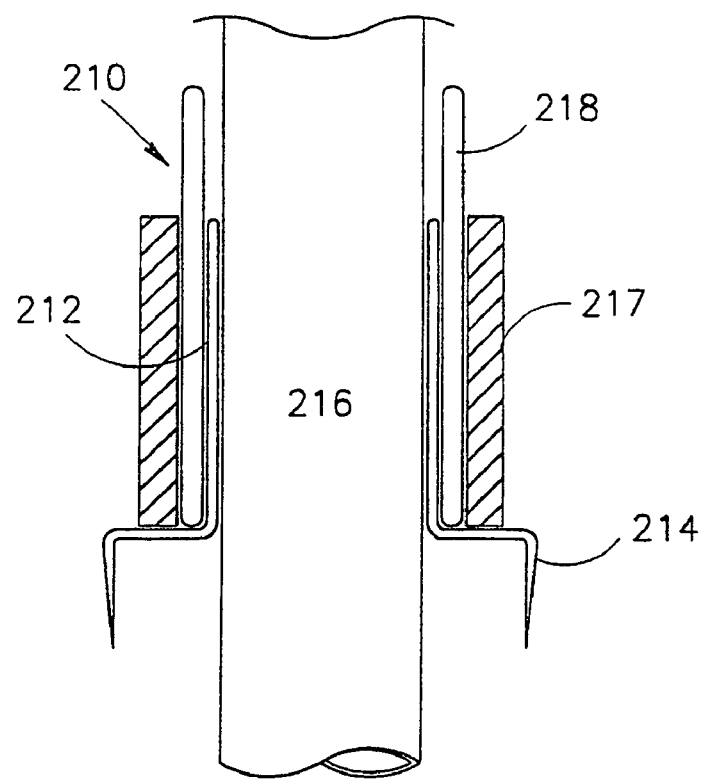
FIGS. 6B and 6C illustrate the deployment of a variant of the device of FIG. 6A.
Figure 6C:
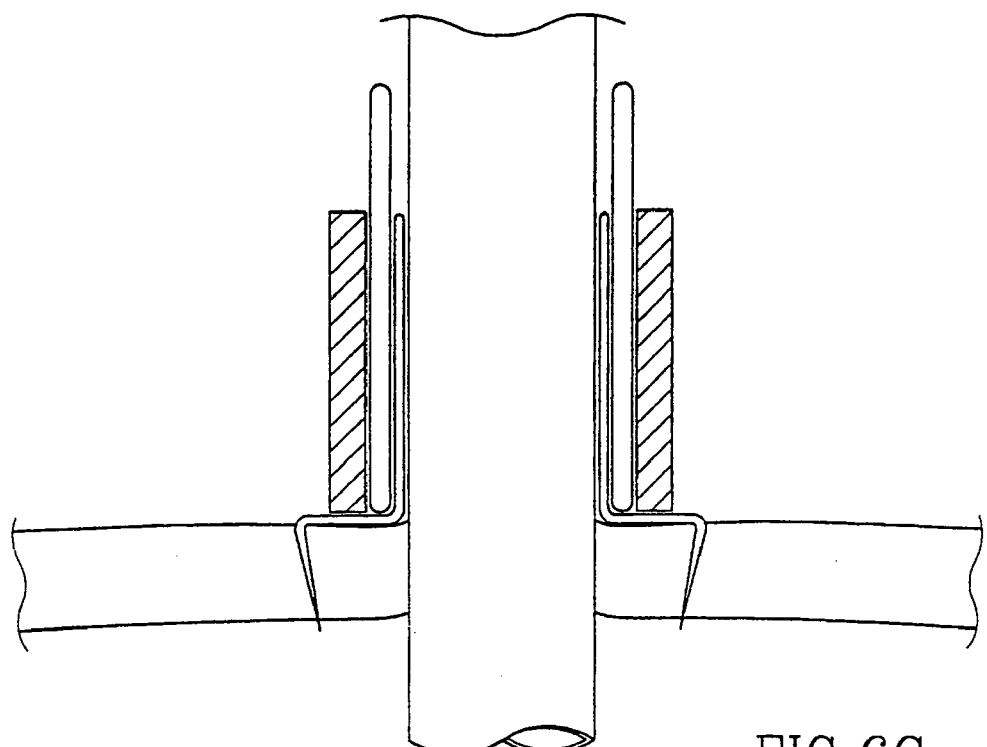

FIG. 6B illustrates a variant of device 210, mounted on catheter 216. In the variant shown, an outer sleeve 217 is provided around ring 212 and an optional balloon 218. In FIG. 6C, device 210 is advanced so that spikes 214 engage the blood vessel. After catheter 216 is removed, device 210 may be collapsed, for example by super-elasticity of the device.

Figure 6D:
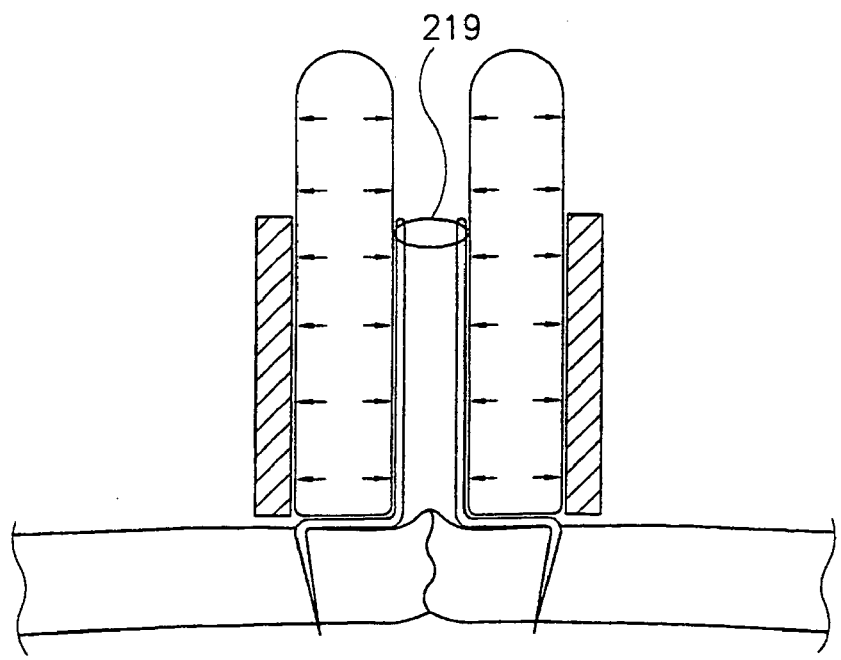
FIG. 6D illustrates sealing a port using a balloon, in accordance with a preferred embodiment of the invention.

FIG. 6D illustrates a method of collapsing using a balloon, in which balloon 218 is inflated against sleeve 217, thereby compressing at least part of ring 212 and causing spikes 214 to move together and seal the hole. In a preferred embodiment of the invention, the part of ring 212 (actually a sleeve) which is further from the blood vessel is made more rigid so that the collapsing of the ring is more pronounced nearer the vessel. Alternatively or additionally, ring 212 may be manufactured to selectively rigid and ductile at different axial locations thereof, preferably so that pans of the ring along the same axial line as spikes will distort more, concentrating the effect on the spikes. Alternatively or additionally, a portion 219 of the ring, preferably at its far end, is made substantially rigid, so that it can act as a pivot for urging the spikes together. As a result, the axial length of ring 210 is preferably reduced. Alternatively or additionally, by allowing different relative radial compression along the ring, balloon 218 better engages device 210 and is less likely to slip off during the inflation.

The embodiment of FIG. 6 is an example where a combination of elastic and plastic distortion may be useful. Elastic (passive) distortion to close the hole to substantially eliminate any blood leaking after catheter 216 is removed, for example by the base of the ring collapsing and a further sealing of the hole by plastic distortion of more distal portions of the rings, to ensure a complete seal.

With reference to portion 219 it is noted that portion 219 can serve as a pivot (as in FIG. 4) for a different type of lever, one in which the distal (from the spikes) end of device 210 expands and portion 219 pivots the expansion to urge the spikes together. In one example, portion 219 is between the spikes and the end of the ring and a balloon is inflated inside the end of the ring, rather than outside of it. In another example, the end of the ring may be restrained from resuming an expanded position by sleeve 217. Once the sleeve is removed, the distal end of the ring expands and causes the spikes to collapse towards each other.

In some embodiments of the invention, portion 219 (or pivot 368 of FIG. 4) may be provided as a movable element, being part of the port or being provided as an external restraint. Thus, by selectively locating the pivot and the location at which force is applied to the device, various configurational changes may be achieved.

Alternatively or additionally, sealer 210 utilizes a double action mechanism. The sealer is provided at a diameter similar to that of catheter 216. A first activation of the sealer causes spikes 214 to extend outwards, as shown in FIG. 6A. A second activation of the sealer causes the spikes to move towards each other. These activations can be by passive, active and/or triggered distortion mechanisms. As can be appreciated, in some embodiments of the invention, ring 212 is not required to be a complete ring. For example, ring 212 can formed of a plurality of abutting parallelograms.

Figure 7:
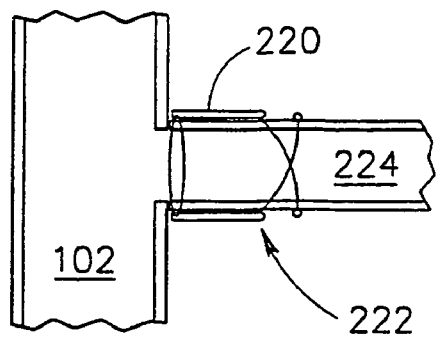
FIG. 7 illustrates a port sealer, in which the sealer cuts off a portion of a blood vessel while performing the seal.

FIG. 7 illustrates a port sealer 220 in which the sealer cuts off a portion of a blood vessel (or graft, electrode, wire or other tube) 224 which is connected to vessel 102. In the example of FIG. 7, an iris cutter 222 pinches, cuts and/or seals vessel 224. Possibly two sets of irises 222 are provided, one to seal and one to cut off. This type of seal (and the one of FIG. 6) is especially suitable for correcting a failed anastomosis. Possibly, the application of pressure using a balloon, as in FIG. 6D, is performed only if necessary (i.e., a leak). Additionally, such a port (or suitable variations of the ports described herein) may be used for vessel ends, for example during certain types of bypass procedures using mammary arteries. In a particular embodiment, iris 222 comprises a plurality of hard leaves which lay flat against the inner surface of the lumen of the port. When an inner restraint is removed, these leaves fold inwards, sealing the enclosed blood vessel and/or severing it. This type of mechanism, as well as others described herein, can also be used to seal an end of a blood vessel, rather than a side thereof.

FIGS. 8A-8B illustrates a hole sealer 230 in which the sealer is not in the same plane of the surface of the blood vessel and in which it is possible to avoid any contact between the sealer and the blood flow. FIG. 8A illustrates sealer 230 in an open configuration, in which vessel 102 is engaged by a plurality of spikes 234. FIG. 8B illustrates sealer 230 in a closed configuration, in which a pressure ring (or members) 232 pinch vessel 102 forming a seal, so that there is no contact between the blood flow and sealer 230.

Figure 8D:
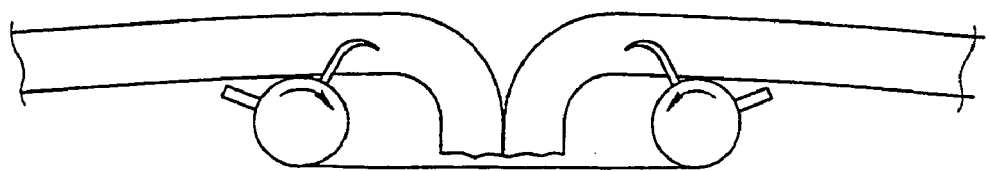

FIGS. 8C and 8D illustrate a port sealing device 350 suitable for closing a hole without any contact with the blood flow. Device 350 comprises a ring 352, preferably a torus, having thereon a plurality of spikes 354. One or more protrusions 356 are preferably formed on the ring and are preferably engaged by a holder 358 with a track that preferably matches the protrusions.

When holder 358 is retracted, ring 352 distorts (preferably elastically, super elastically or based on a shape memory) around its median axis, as shown in FIG. 8D, so that spikes 354 engages the vessel and urge it closed. Alternatively or additionally, ring 352 may collapse or otherwise distort so that it has a reduced radius or at least to cause the spikes to move towards each other.

In a preferred embodiment of the invention, device 350 acts as a fail safe for vascular surgery. If holder 358 is disturbed or otherwise slips off of protrusions 356, the device seals the hole in the blood vessel. the hole can be reopened using a suitable tool which distorts the configuration of FIG. 8D back to the configuration of FIG. 8C. In a preferred embodiment of the invention, a second plurality of spikes 353 is provided which spikes engage the vessel, so that device 350 will stay attached to the vessel rather than to the holder, of the holder moves.

Figure 8E:
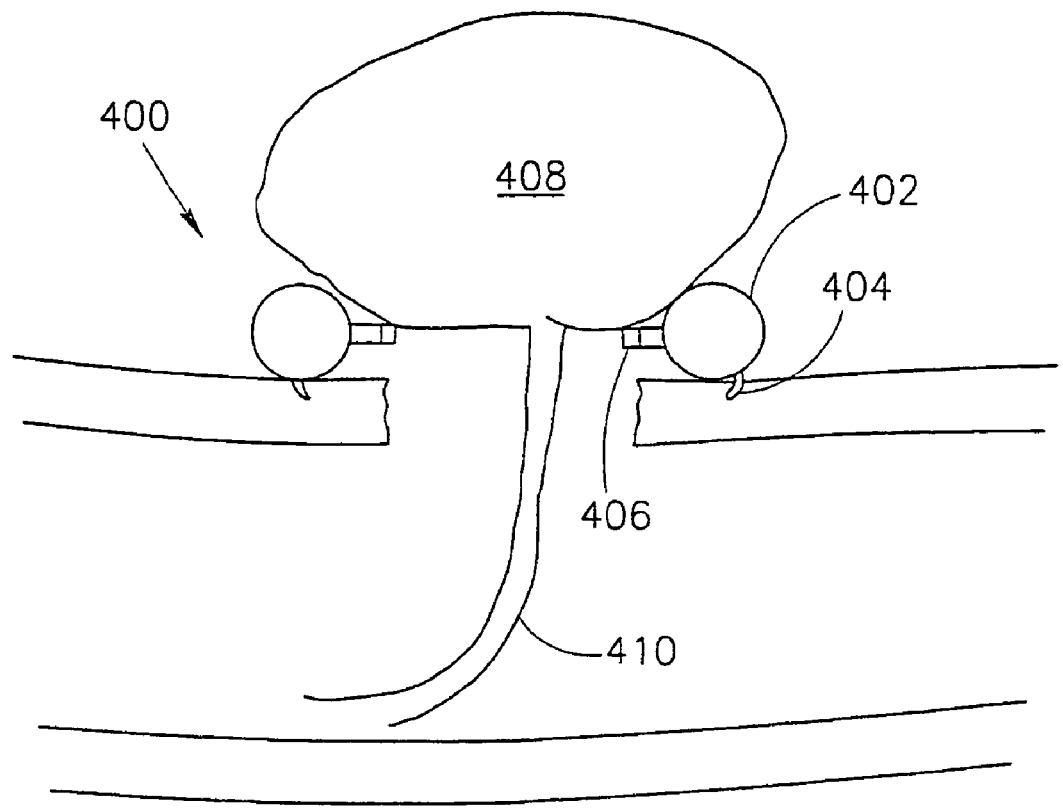
FIG. 8E illustrates a hole sealer which is provided to an outside of a blood vessel from inside of the blood vessel, in accordance with a preferred embodiment of the invention.

In a preferred embodiment of the invention, a port device is attached to a blood vessel from inside the blood vessel. For example, if device 350 is super-elastic, it can be radially compressed so that it can be provided through the hole, while maintaining it in the configuration of FIG. 8C, by engaging protrusions 356. FIG. 8E shows such a deployment of a device 400. In a preferred embodiment of the invention, device 400 is pushed out of the blood vessel while being maintained in a compressed configuration, so that it fits through the hole. This can be achieved by providing it through a catheter (not shown). Once the device is outside the blood vessel, a balloon 408 is inflated so that it engages a plurality of protrusions 406 (similar in function to protrusions 356), to prevent the device from closing the hole. Alternatively, a tube may be passed through the lumen of device 400 to provide a working channel and this tube may include indentations, protrusions, an inflatable cuff or other means to engage the protrusions. Balloon 408 can also be used to force device 400 against the blood vessel so that spikes 404 (or other spikes, not shown) engage the blood vessel. when the balloon is deflated, the device distorts and the hole closes. The balloon, in its deflated state is preferably pulled out through the hole.

Figure 9A:
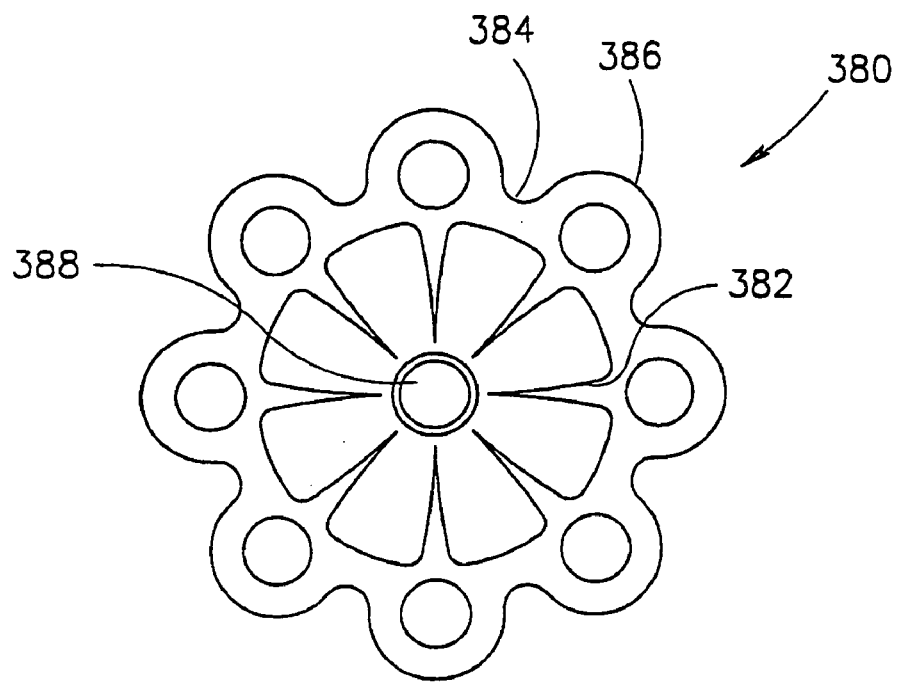
FIG. 9A illustrates a port sealer whose configuration is modified using one or more threads, in accordance with a preferred embodiment of the invention.

FIG. 9A illustrates a port 380, which is distorted using threads. Device 380 has a plurality of spikes 382 arranged on a ring 384. In addition, a plurality of anchors (for threads) 386 are provided, for example holes. During deployment, spikes 382 are bent forward (into the figure plane) to engage a blood vessel. Possibly, this bending is achieved by folding the anchors 386 up out of the figure plane. This distortion may be plastic or elastic. A loop of thread is preferably threaded through each one of anchors 386. When sealing the port, the loops are all pulled towards the center of the device, for example if the other side of the loop is threaded through a ring 388 (not part of the port). Thus, the port collapses and becomes sealed.

Figure 9B:
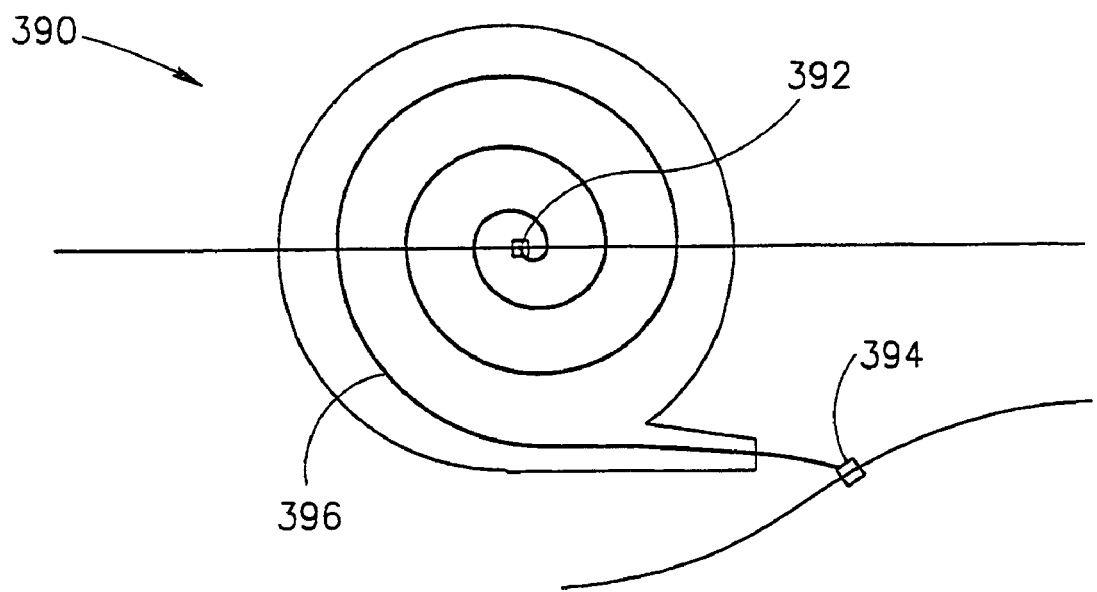
FIG. 9B schematically illustrates a thread retractor, in accordance with a preferred embodiment of the invention.

FIG. 9B schematically illustrates a thread retractor 390, in accordance with a preferred embodiment of the invention. A first thread from a purse string stitch is attached to an anchor 392. A second thread is attached to an anchor 394, which is at the end of a retractor 396, for example a spiral spring as shown. When the purse-string stitch is performed, device 390 is preferably connected to the ends of the threads, either near the stitch, for example inside the body or further away, such as outside the body. Thus, various sizes of device 390 may be used. If a tube is inadvertently removed from the purse string, retractor 396 is able to pull the thread and close the hole, preventing sever blood loss. Preferably, the tension in the retractor is selected to be large enough to pull the purse-string closed but not so large that it damages the vessel at the points where the thread is connected. Preferably, anchor 392 and/or anchor 394 is a ratchet anchor, which allow the movement of thread only in one direction, so that threading the anchors is easier.

The above description has focused on temporary ports and anastomosis devices. However, it should be noted that the same or similar devices can be used for sealing holes and/or making other repairs in blood vessels. Such a sealer can be provided over a catheter which is inserted into a hole. The catheter preferably comprises inflatable cuffs which can be used to block blood flow from the damaged area while the sealing is being performed.

Additionally, the above devices can be used for inserting a small diameter wire or tube into and/or out of a blood vessel. Typically, a relatively large diameter catheter is required for guiding the wire to its destination. In some cases, the wire may have a larger tip, for example a sensor or a pacing electrode. In a preferred embodiment of the invention, the wire and catheter are provided through a port as described herein. When the catheter is retracted the port is sealed, on the wire. Preferably, the seal is also utilized to stabilize the position and/or rotation of the wire.

A different use for passing a wire through a seal of the port is to ease the reopening of the port. As indicated above, some types of ports can be opened after they are sealed. In a preferred embodiment of the invention, the wire is coupled to the port. When it is desired to open the port, a catheter is guided over the wire to the port. Preferably, a greater contra-force on the port can be generated by pulling on the wire while advancing the catheter. Thus, there is also less danger of applying force against a part of vessel 102 opposite the port. If the wire passes through the seal, in a preferred embodiment of the invention, the catheter is advanced along the wire until it passes through the port. Alternatively or additionally, pulling on the wire distorts the port so that it opens, is easier to open or is able to be opened, from the force of the catheter against it. In some embodiments, the wire is attached to the portion of the port which is outside the blood vessel.

It should be appreciated that many of the structures described herein may also be applied to other invasive and/or implantable devices, beyond those used for anastomosis, especially such devices which are inflatable, expandable and/or otherwise deployed. However, as will be appreciated, that some of the above described structures solve particular problems of port sealing, for example functioning as a port and sealing a hole in a blood vessel.

It will be appreciated that the above described methods of applying a vascular port and sealing a hole may be varied in many ways, including, changing the order of steps and the methods of distortion used. In addition, a multiplicity of various features, both of method and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. Also within the scope of the invention are surgical kits which include sets of medical devices suitable for making a single or a small number of ports or sealing holes of various sizes. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

The invention claimed is:

1. A device for sealing a hole in a blood vessel, comprising:
   a blood vessel engager comprising at least one spike, the blood vessel engager being adapted to engage a portion of a blood vessel adjacent a hole in the blood vessel between the lumen of said blood vessel and a tissue surrounding said blood vessel; and
   a body coupled to the blood vessel engager,
   wherein said device is adapted to have at least two configurations in which the blood vessel engager engages the blood vessel, a first configuration in which said device does not seal the hole and a second configuration in which said device seals said hole in the blood vessel, in a manner which substantially eliminates any blood leakage through the hole.

2. A device according to claim 1, wherein said body defines a device lumen therethrough.

3. A device according to claim 2, wherein said device comprises a second blood vessel engager for engaging a second blood vessel, such that the device can selectively perform an anastomosis between said blood vessel and said second blood vessel or seal said blood vessel.

4. A device according to claim 2, wherein said device lumen is adapted to receive a tube therein, which device lumen closes around said tube.

5. A device according to claim 4, wherein said body is adapted to be radially compressed to perform said closing of the device lumen around the tube.

6. A device according to claim 4, wherein said device lumen is adapted for multiple insertions and removals of said tube.

7. A device according to claim 4, wherein said device lumen self-seals after said tube is removed.

8. A device according to claim 2, wherein said device lumen is sealed in said second configuration, by said device.

9. A device according to claim 1, wherein said body defines said device lumen therethrough and wherein said device is arranged to form said hole in said vessel.

10. A device according to claim 1, wherein said at least one spike is arranged to engage said vessel after said hole has a final diameter suitable for insertion of a medical tube therethrough.

11. A device according to claim 1, wherein said at least one spike is arranged to engage said vessel while the size of the hole is adjusted for insertion of a medical tube therethrough.

12. A device according to claim 1, wherein said at least one spike is arranged to engage said vessel while the hole is formed.

13. A device according to claim 1, wherein in the second configuration the body is distorted relative to the first configuration.

14. A device according to claim 1, wherein in the second configuration said at least one spike is distorted relative to the first configuration.

15. A device according to claim 1, wherein said body comprises a ring.

16. A device according to claim 1, wherein said body comprises a hollow cylinder.

17. A device according to claim 1, wherein in said second configuration, said at least one spike urges a first portion of said blood vessel against a second portion of said blood vessel, to seal said hole.

18. A device according to claim 17, wherein said device is arranged so that intimas of said two blood vessel portions are urged against each other to form said seal, by a configuration change between the first and second configurations.

19. A device according to claim 1, wherein said device is arranged so that in said second configuration, said at least one spike urges a first portion of said blood vessel against a portion of said device, to seal said hole.

20. A device according to claim 1, wherein said device is arranged so that in said second configuration, a first portion of said device is urged against a second portion of said device, to seal said hole.

21. A device according to claim 1, wherein said device is adapted to be attached to a side of a blood vessel.

22. A device according to claim 1, wherein said device is adapted to be attached to an end of a blood vessel.

23. A device according to claim 1, wherein said device is adapted to seal said hole and to remain in a body after a wound for accessing said device, is closed.

24. A device according to claim 1, wherein the blood vessel engager and the body are sized and shaped to engage a femoral artery.

25. A device according to claim 1, wherein the blood vessel engager includes more than three spikes.

26. A device according to claim 1, wherein the blood vessel engager includes at least six spikes.

27. A device according to claim 1, wherein the device is adapted to move to the second configuration upon removal of an obstructer which prevents movement from the first configuration to the second configuration.

28. A device according to claim 1, wherein the device is adapted to change between the at least two configurations by itself.

29. A device according to claim 28, wherein said at least one spike does not distort when changing between said first and second configurations.

30. A device according to claim 28, wherein said configuration change comprises a star distortion in which a circular profile of said body changes to a star profile.

31. A device according to claim 28, wherein said configuration change comprises a rotational distortion in which a donut shaped body distorts around its median axis.

32. A device according to claim 1, wherein the device is adapted to seal the hole in the second configuration by forcing portions of the device against each other.

33. A device according to claim 1, wherein the device is adapted to seal the hole in the second configuration by forcing portions of the blood vessel against each other.

34. A device for sealing a hole in a blood vessel, comprising:
   a blood vessel engager comprising at least one spike, for engaging a portion of a blood vessel adjacent a hole in the blood vessel between the lumen of said blood vessel and a tissue surrounding said blood vessel; and
   a body coupled to the blood vessel engager,
   wherein said device is adapted to have at least two configurations, a first configuration in which said, device does not seal the hole and a second configuration in which said device seals said hole,
   wherein said body comprises a detachable portion which portion is removed prior to closing said wound.

35. A method of providing a tool in a blood vessel of a patient, comprising:
   attaching a port to the blood vessel;
   using said port to access said blood vessel;
   sealing said port, such that no blood flows through said port; and
   leaving said sealed port attached to said blood vessel for at least two weeks, wherein said port is completely enclosed by flesh of the patient.

36. A method according to claim 35, wherein removing a tube from said port causes said port to seal.

37. A device for sealing a hole in a blood vessel, comprising:
   a blood vessel engager comprising at least four spikes, for engaging a portion of a blood vessel adjacent a hole in the blood vessel; and
   a body coupled to the blood vessel engager,
   wherein said device is adapted to have at least two configurations in which the blood vessel engager engages the blood vessel, a first configuration in which said device does not seal the hole and a second configuration in which said device seats said hole.

38. A device according to claim 37, wherein said body includes a valve for moving the device between the first and second configurations.

39. A device according to claim 37, wherein said device is arranged to change configuration with less applied force, after removal of a tube from the device lumen.

40. A device for sealing a hole in a blood vessel, comprising:
   a blood vessel engager comprising at least one spike, the blood vessel engager being adapted to engage a portion of a blood vessel adjacent a hole in the blood vessel; and
   a body coupled to the blood vessel engager,
   wherein said device is adapted to have at least two configurations, a first configuration in which said device does not seal the hole and a second configuration in which said device seals said hole in the blood vessel, in a manner which substantially eliminates any blood leakage through the hole,
   wherein said body defines a device lumen therethrough.

41. A device according to claim 40, wherein the blood vessel engager includes more than three spikes.

42. A device according to claim 40, wherein the device is adapted to move to the second configuration by elastic distortion of at least part of the device.

43. A device according to claim 40, wherein the body has an outer zigzag endless contour.

44. A device according to claim 40, wherein in the second configuration the body and spikes are included together in a flat plane.

45. A device according to claim 40, wherein in the first configuration the spikes are oriented substantially parallel to an axis of the device lumen.

46. A device according to claim 40, wherein in the second configuration the spikes are oriented substantially toward the device lumen.

47. A device according to claim 40, wherein the body comprises a plurality of looped elements.

48. A method of closing a hole in a blood vessel, comprising:
attaching at least one, spike of a sealing device to a blood vessel, adjacent a hole in the blood vessel, in a first configuration in which the hole is not sealed; and
changing a configuration of the sealing device, while the at least one spike engages the blood vessel, to a second configuration in which the sealing device seals the hole.

49. A method according to claim 48, wherein changing the configuration comprises self distortion of the scaling device, upon removal of an obstructer preventing the configuration change.

50. A method according to claim 48, comprising inserting a tool through the hole into the blood vessel after attaching the at least one spike and before changing the configuration to seal the hole.

51. A device for sealing a hole in a blood vessel, comprising:
an annular engager having a perimeter of approximately a hole in a blood vessel; and
at least one spike configured for being substantially parallel to an axis of the center of said annular engager, said annular engager being configured to be disposed with said at least one spike turned toward the internal space thereof.

52. The device of claim 51, wherein said annular engager is configured to be disposed to seal said hole.

53. The device of claim 52, wherein said annular engager is adapted to be disposed on an extravascular portion of said blood vessel.

54. The device of claim 52, wherein said annular engager is adapted to be disposed on an intravascular portion of said blood vessel.

55. The device of claim 53, wherein said disposing comprising stapling the hole.

56. The device of claim 55, wherein said stapling seals said hole, thereby substantially eliminating any blood leakage therethrough.

57. The device of claim 51, wherein said annular engager having at least one curvature being configured for engaging a periphery of said hole.

58. The device of claim 51, wherein said annular engager is a distorted ring having a plurality of curvatures.

59. The device of claim 58, wherein said at least one spike is connected to said distorted ring.

60. A method of for sealing a hole in a blood vessel, comprising:
a) positioning an annular engager having at least one spike adjacent to a hole in an anterior wall of a blood vessel;
b) engaging a periphery of said hole using said at least one spike; and
c) disposing said annular engager adjacent to said hole, thereby sealing said hole.

61. The method of claim 60, wherein said engaging comprising penetrating said periphery of said hole using said at least one spike.

62. The method of claim 60 wherein said positioning is performed using a catheter.

63. A device for sealing a hole in a blood vessel, comprising:
an annular engager having at least one spike, said annular engager being adapted to have a predisposed and a disposed configurations;
wherein in said predisposed configuration said at least one spike being substantially parallel to an axis of the center of said annular engager and in said disposed configuration said at least one spike being turned toward the internal space of said annular engager, said annular engager being configured for engaging a portion of a blood vessel adjacent a hole in the blood vessel in said disposed configuration.

64. The device of claim 63, wherein said annular engager is a undulated ring having a plurality of curvatures.

65. The device of claim 63, wherein said annular engager is configured to be in said predisposed configuration when it is mounted on a catheter.

66. The device of claim 63, wherein in said disposed configuration, said at least one spike urges a first portion of said blood vessel against a second portion of said blood vessel, to seal said hole.

67. The device of claim 66, wherein said device is arranged so that intimas of said first and second portions are urged against each other to form said seal, by a configuration change between the predisposed and disposed configurations.

68. The device of claim 63, wherein said device is arranged so that in said disposed configuration, a first portion of said device is urged against a second portion of said device, to seal said hole.

69. The device of claim 63, wherein said annular engager and the body are sized and shaped to engage a femoral artery.

70. The device of claim 63, wherein said annular engager includes more than three spikes.

71. The device of claim 63, wherein said annular engager includes at least six spikes.

* * * * *